United States Patent
Kim et al.

(10) Patent No.: US 8,874,195 B2
(45) Date of Patent: Oct. 28, 2014

(54) APPARATUS AND METHOD FOR HEALTH CARE

(75) Inventors: Youn-ho Kim, Hwaseong-si (KR); Kun-soo Shin, Seongnam-si (KR); Hyung-sok Yeo, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 2309 days.

(21) Appl. No.: 11/480,855

(22) Filed: Jul. 6, 2006

(65) Prior Publication Data

US 2007/0027395 A1 Feb. 1, 2007

(30) Foreign Application Priority Data

Jul. 28, 2005 (KR) ........................ 10-2005-0069113

(51) Int. Cl.
| | |
|---|---|
| *A61B 5/04* | (2006.01) |
| *G06F 19/00* | (2011.01) |
| *A61B 5/00* | (2006.01) |
| *A61B 5/11* | (2006.01) |
| *A61B 5/0402* | (2006.01) |
| *A61B 5/01* | (2006.01) |
| *A61B 5/0456* | (2006.01) |
| *A61B 5/024* | (2006.01) |
| *A61B 5/145* | (2006.01) |

(52) U.S. Cl.
CPC ........ *A61B 5/0402* (2013.01); *A61B 2562/0219* (2013.01); *G06F 19/3431* (2013.01); *A61B 5/01* (2013.01); *A61B 5/4866* (2013.01); *A61B 5/1123* (2013.01); *A61B 5/1118* (2013.01); *A61B 5/0456* (2013.01); *A61B 5/02416* (2013.01); *A61B 5/4884* (2013.01); *A61B 5/145* (2013.01)
USPC ........................................... 600/509

(58) Field of Classification Search
CPC ........................................ A61B 5/00
USPC ........................... 600/509, 546, 595
See application file for complete search history.

(56) References Cited

U.S. PATENT DOCUMENTS

| | | | |
|---|---|---|---|
| 5,511,553 A | 4/1996 | Segalowitz | |
| 6,026,321 A | 2/2000 | Miyata et al. | |
| 6,496,715 B1 * | 12/2002 | Lee et al. | 600/424 |
| 2003/0083559 A1 | 5/2003 | Thompson | |
| 2006/0161079 A1 * | 7/2006 | Choi et al. | 600/595 |
| 2007/0276271 A1 * | 11/2007 | Chan | 600/509 |

FOREIGN PATENT DOCUMENTS

| | | |
|---|---|---|
| JP | 5-76501 | 3/1993 |
| JP | 6-181891 | 7/1994 |

* cited by examiner

*Primary Examiner* — Eric D. Bertram
(74) *Attorney, Agent, or Firm* — Staas & Halsey LLP (57) ABSTRACT

A health care apparatus and method thereof. The health care apparatus comprises: a sensing position determining unit determining a body part of an examinee where vital signals of the examinee are sensed; a vital potential sensing unit sensing potential signals of the examinee corresponding to a determined result; and an analyzing unit analyzing the sensed result. Accordingly, the health care apparatus can determine body parts by itself and senses potential signals corresponding to the body parts to calculate reliable measurements without information of the body parts to which the health care apparatus is attached. Furthermore, the health care apparatus can be easily attached to the body compared to a conventional health care apparatus, and can calculate a health index reflecting the present behavior pattern of the examinee. The health care apparatus can also determine the health state of local body parts of the examinee and inform the examinee of the calculated health indexes on a real-time basis.

17 Claims, 9 Drawing Sheets

APPARATUS AND METHOD FOR HEALTH CARE

CROSS-REFERENCE TO RELATED APPLICATION

This application claims the benefit of Korean Patent Application No. 10-2005-0069113, filed on Jul. 28, 2005 in the Korean Intellectual Property Office, the disclosure of which is incorporated herein by reference.

BACKGROUND OF THE INVENTION

1. Field of the Invention

The present invention relates to a method and apparatus for health care, and particular, to a method and apparatus for health care in which vital signals of an examinee are examined and potential signals corresponding to the examined result are sensed and analyzed to determine a body state of the examinee.

2. Description of Related Art

Examples of vital signals that can be sensed from an examinee are electrocardiogram (ECG) signals and electromyogram (EMG) signals. ECG signals can be used to determine whether the heartbeat of the examinee is normal and how much stress the examinee has. EMG signals can be used to determine the amount of consumed calories according to the amount of movement of the examinee. ECG signals and EMG signals are examples of vital signals.

A conventional health care apparatus determines the body state of the examinee using vital signals sensed from the examinee. That is, health indexes of the examinee are calculated using the sensed vital signals. The health indexes may be heart rate, heart stress, balance of the autonomic nerve system, amount of consumed calories, blood pressure, and core temperature.

However, conventional health care apparatuses cannot calculate health indexes reflecting the present body state. For example, in a conventional health care apparatus in which the acceleration of an examinee is sensed and the amount of consumed calories of the examinee is calculated using the sensed result, the consumed amounts of calories of two examinees, one of whom rides an uphill road exhausted on a bicycle and the other rides the uphill road easily with the same acceleration, are calculated as equal.

In addition, the conventional health care apparatus cannot calculate the accurate health index without information about the body part to which the health care apparatus is attached. For example, if attached to the chest of the examinee, the apparatus may sense an ECG signal, and if attached to a thigh of the examinee, the apparatus may sense an EMG signal. However, if no information about the attached part of the body is provided, the apparatus senses both the ECG signal and the EMG signal and thus cannot calculate an accurate health index.

Also, the conventional health care apparatus that comprises a plurality of devices must be attached to several body parts, thus making it inconvenient for the examinee.

Furthermore, the conventional health care apparatus cannot determine the local body state of the examinee, and inform the measurements of the health indexes to the examinee on a real-time basis.

BRIEF SUMMARY

An aspect of the present invention provides a health care apparatus in which body parts where vital signals of an examinee are examined and potential signals corresponding to the examined result are sensed and analyzed to determine a body state of the examinee.

An aspect of the present invention also provides a method of providing health care including examining a body part where vital signals of an examinee are sensed, sensing a potential signal corresponding to the examined result, and analyzing the sensed result to determine a body state of the examinee.

An aspect of the present invention also provides a computer-readable recording medium for storing a computer program for executing a method including examining a body part where vital signals of an examinee are sensed, sensing a potential signal corresponding to an examined result, and analyzing the sensed result to determine a body state of the examinee.

According to an aspect of the present invention, there is provided a health care apparatus including: a sensing position determining unit determining a body part of an examinee where vital signals of the examinee are sensed; a vital potential sensing unit sensing potential signals of the examinee corresponding to a determined result; and an analyzing unit analyzing the sensed result.

The health care apparatus may further comprise a health index calculating unit calculating a desired health index using an analyzed result and, wherein the health index is an index indicating a body state of the examinee.

The sensing position determining unit may includes: an examining unit examining whether an acceleration of the body part meets a predetermined magnitude; and a body part determining unit determining the body part in response to the examined result.

The sensing position determining unit may include: an examining unit examining whether a predetermined vital signal is sensed in the body part; and a body part determining unit determining the body part in response to the examined result.

The vital potential sensing unit may sense the vital signals of the examinee corresponding to the determined result.

The vital potential sensing unit may include: a vital signal sensing unit sensing the vital signals of the examinee in response to the determined result; and a filtering unit filtering the sensed vital signals in response to the determined result and outputting the filtered vital signals as the potential signals.

The vital potential sensing unit may further include a sensing mode determining unit determining sensing modes in response to the determined result, and wherein the vital signal sensing unit and the filtering unit operate according to the determined sensing modes.

The vital potential sensing unit may further include a matching unit in which information about the vital signals is matched to the determined result, and wherein the vital signal sensing unit senses the vital signals expressed in the vital signal information matched to the determined result.

The vital potential sensing unit may further include a matching unit in which information about the filtering is matched to the determined result, and the filtering unit filters the sensed vital signals according to the filtering information matched to the determined result.

The vital potential sensing unit may be formed of one or more sensing devices attached to the body of the examinee and the one or more sensing devices may be formed in a single body or separately connected to each other in a network.

The potential signal may be a vital signal having a frequency band corresponding to the determined result among the vital signals that can be sensed from the examinee.

The vital signal sensing unit may sense electrocardiogram (ECG) signals or electromyogram (EMG) signals of the examinee in response to the determined result.

The health care apparatus may further include a user interface unit providing a user interface displaying at least one of the analyzed result and the calculated health index.

The health care apparatus may further include a health state notifying unit that functions corresponding to the calculated health index to inform the examinee about a health state of the examinee.

The health state notifying unit may inform the examinee about the health state of the examinee using one of a visual path, a hearing path, and a tactual path.

The health index may be one selected from the group consisting of heart rate, heart stress, balance of the autonomous nervous system, amount of consumed calories, blood pressure and core temperature.

According to another aspect of the present invention, there is provided a method for providing health care including: determining a body part of an examinee where vital signals of the examinee are sensed; sensing potential signals of the examinee corresponding to a determined result; and analyzing the sensed result.

The method may further include calculating a health index using an analyzed result, wherein the health index is an index indicating a health state of the examinee.

The sensing the potential signals may include: sensing the vital signals of the examinee corresponding to the determined result; and filtering the sensed vital signals according to the determined result, and wherein the filtering result is the potential signal.

The sensing the potential signals may include: determining sensing modes according to the determined result; sensing vital signals of the examinee according to the determined sensing modes; and filtering the sensed vital signals according to the determined sensing modes, and wherein the filtering result is the potential signal.

The sensing the vital signals may include: determining whether the determined body part is in the upper body of the examinee; and when the determined body part is in the upper body of the examinee, sensing ECG signals of the examinee.

The sensing the vital signals may include: determining whether the determined body part is in the upper body of the examinee; and sensing EMG signals of the examinee when the determined body part is not in the upper body of the examinee.

The method may further include displaying at least one of the analyzed result and the calculated health index.

The determining whether the determined body part is in the upper body may include: sensing all of the vital signals that can be sensed from the body part; filtering the sensed vital signal through a filter having a transmittance frequency band between about 5 Hz to 30 Hz; detecting an R-peak value from the filtered vital signal; and calculating a time difference between a present time of the detected R-peak value and a time point of a previously-detected R-peak value.

According to another aspect of the present invention, there is provided a computer-readable recording medium storing a program for executing the aforementioned method.

Additional and/or other aspects and advantages of the present invention will be set forth in part in the description which follows and, in part, will be obvious from the description, or may be learned by practice of the invention

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF EMBODIMENTS

Reference will now be made in detail to embodiments of the present invention, examples of which are illustrated in the accompanying drawings, wherein like reference numerals refer to the like elements throughout. The embodiments are described below in order to explain the present invention by referring to the figures.

Figure 1:
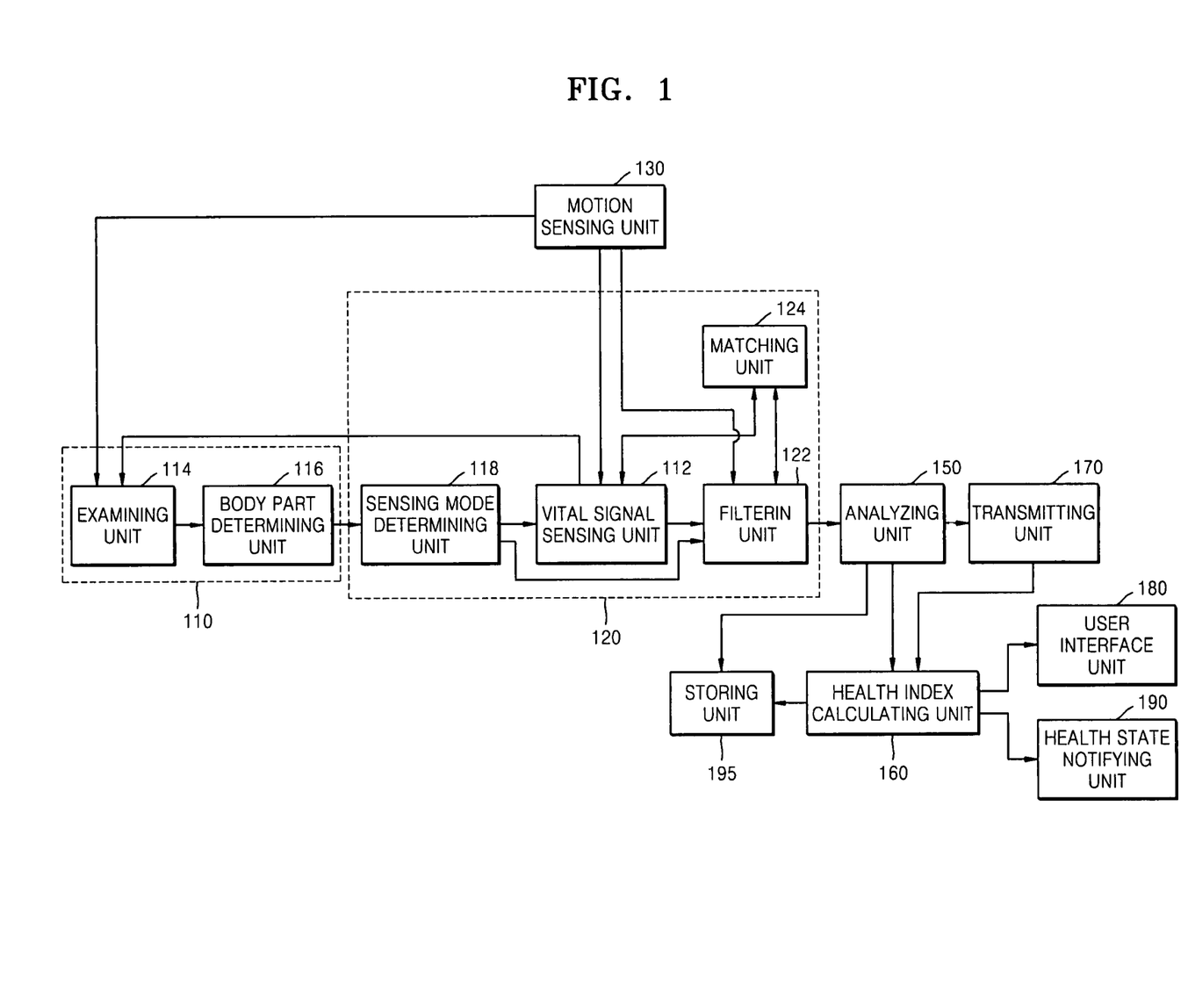
FIG. 1 is a block diagram of a health care apparatus according to an embodiment of the present invention.

FIG. 1 is a block diagram of a health care apparatus according to an embodiment of the present invention. The health care apparatus includes a sensing position determining unit 110, a vital potential sensing unit 120, a motion sensing unit 130, an analyzing unit 150, a health index calculating unit 160, a transmitting unit 170, a user interface unit 180, a health state notifying unit 190, and a storing unit 195. The sensing position determining unit 110 includes an examining unit 114 and a body part determining unit 116 and the vital potential sensing unit 120 includes a viral signal sensing unit 112, a sensing mode determining unit 118, a filtering unit 122, and a matching unit 124.

The sensing position determining unit 110 examines body parts where vital signals of the user are sensed. Also, the vital potential sensing unit 120 senses a potential signal of the examinee corresponding to the examined result of the sensing position determining unit 110.

The potential signal may be a vital signal having a frequency band corresponding to the examined result of the sensing position determining unit 110 among the sensible vital signals.

The motion sensing unit 130 senses a behavior pattern of the examinee. That is, the motion sensing unit 130 senses a movement of the examinee over a period of time. The motion sensing unit 130 can be formed of a plurality of sensing devices.

The sensing devices can be formed in a single body. If the sensing devices are formed in one defined area, they can be referred to as a single body. For example, if a plurality of sensing devices are provided in one patch, the sensing devices can be regarded as a single body.

The sensing devices can also be formed separately in a network. That is, the sensing devices can be distributed in several body parts of the examinee. In this case, the sensing devices can be disposed in the same network.

One of the sensing devices may function as an acceleration sensor and an angular velocity sensor. The acceleration sensor senses acceleration in x, y and z directions. The angular velocity sensor senses the angular velocity of the examinee. The angular velocity sensor is also called a gyro sensor.

The movements that are sensed over time by the motion sensing unit 130 are taking a rest, walking, and running. However, taking a rest, walking, and running are examples of the motions that can be sensed by the motion sensing unit 130, and there may also be other types of movement.

When the motion sensing unit 130 distinguishes the movements as taking a rest, walking, and running, a standard for distinguishing the motions as taking a rest, walking, and running of the sensed results must be defined in advance.

Hereinafter a vital signal sensing unit 112, an examining unit 114, a body part determining unit 116, a sensing mode determining unit 118, a filtering unit 122, and a matching unit 124 will be described to describe the sensing position determining unit 110, the vital potential sensing unit 120, and the motion sensing unit 130 can be described more specifically.

The health care apparatus according to the current embodiment of the present invention can sense one or more vital signals of an examinee, and calculates one or more health indexes using the sensed vital signals.

The vital signals may include a photo-pletysmography (PPG) signal, an electrocardiogram (ECG) signal, and an electromyogram (EMG) signal.

The health indexes may be heart rate, heart stress, balance of the autonomic nervous system, amount of consumed calories, blood pressure, and core temperature.

Specifically, the health care apparatus according to the current embodiment may use ECG signals sensed from the examinee to calculate health indexes such as the heart rate, the heart stress, and the balance of the autonomic nervous system. Also, the health care apparatus according to the current embodiment may use the EMG signals to calculate health indexes such as the amount of consumed calories, or both the PPG signals and the ECG signals to calculate the blood pressure of the examinee.

The health care apparatus according to the current embodiment of the present invention may be provided in a plurality of separate devices connected to each other in a network, or can be provided in one device.

In particular, a health care apparatus formed in one device, can be attached to the body of the examinee. For this, the health care apparatus can be provided in a medium such as a patch which can be attached to and detached from a body.

The vital signal sensing unit 112 senses a vital signal of the examinee. The vital signal sensing unit 112 can sense all the sensible vital signals from the body parts where the vital signal sensing unit 112 is attached to. When the health care apparatus is formed in a device attached to the body, the vital signal sensing unit 112 can sense all the sensible vital signals from the body parts to which the health care apparatus is attached.

The motion sensing unit 130 senses an acceleration of the body parts from which the vital signals are sensed by the vital signal sensing unit 112. The examining unit 114 examines whether the sensed acceleration of the body parts is predetermining. That is, when the health apparatus is provided in a device attached to the body as described above, the examining unit 114 examines whether the acceleration of the body parts to which the health care apparatus is attached is predetermined.

For example, when an examinee is riding a bicycle, since the acceleration of the lower body is more active than the upper body, the degree of activity of acceleration which distinguishes the upper body and the lower body can be calculated in advance, and the examining unit 114 examines the "degree of activity of the acceleration" sensed in the motion sensing unit 130 by comparing it with the calculated value.

The body part determining unit 116 responds to the examined result of the examining unit 114 and thus can determine whether it is the upper body or the lower body where vital signals are sensed by the vital signal sensing unit 112. Here, the upper and lower bodies are examples for simplicity of explanation, and the body parts that the body part determining unit 116 can distinguish and determine may be more specific. For example, the body part determining unit 116 can determine whether the body parts in which the vital signals are sensed are the neck, the arms, the chest, or the thighs.

The operations of the examining unit 114 and the body part determining unit 116 described above are also for simplicity of explanation, and can be various as described hereinafter.

That is, the examining unit 114 can examine whether the vital signal sensing unit 112 senses the predetermined vital signals in the body parts. The vital signal sensing unit 112 in the health care apparatus according to an embodiment of the present invention in one device can sense various vital signals according to the body parts to which the health care apparatus is attached.

The sensed vital signals may be mixed with various signals such as ECG signals and EMG signals. However, the signals which are prominent among the mixed signals can vary according to the body parts to which the health apparatus is attached. For example, if the health care apparatus is attached to the chest, ECG signals are prominent among the vital signals sensed by the vital signal sensing unit 112. If the health care apparatus is attached to the thigh, EMG signals are prominent among the vital signals sensed by the vital signal sensing unit 112.

Consequently, as the health care apparatus is formed as one device, the examining unit 114 examines whether the vital signal sensing unit 112 senses the predetermined vital signals in the body parts, and the body part determining unit 116 uses the sensed result to determine which body part the health care apparatus was attached to. The predetermined vital signals may be distinguished according to the body parts.

The sensing mode determining unit 118 determines sensing modes according to the examined body parts. For example, if the body part determining by the body part determining unit 116 is the chest, the sensing mode determining unit 118 determines whether the vital signal sensing unit 112, the filtering unit 122, and the matching unit 124 will operate according to the ECG sensing mode or not. In the ECG sensing mode, the vital signal sensing unit 112 senses the ECG signals in the body parts where the vital signals are sensed.

In the same manner, if the body part determining by the body part determining unit 116 is the thigh, the sensing mode determining unit 118 orders the vital signal sensing unit 112, the filtering unit 122, and the matching unit 124 to operate according to the EMG sensing mode. In the EMG sensing mode, the vital signal sensing unit 112 senses the EMG signals in the body part where the vital signals are sensed.

Consequently, if a sensing mode is determining in the sensing mode determining unit 118, the vital signal sensing unit 112 senses the vital signals in the body part where the vital signals corresponding to the determining sensing mode are sensed.

That is, the vital signals sensed in the vital signal sensing unit 112 operating according to the sensing mode determining in the sensing mode determining unit 118 are part of the vital signals which can be sensed in the sensed body part.

Consequently, the vital signal sensing unit 112 is matched to each body part determining by the body part determining unit 116 to sense the predetermined vital signals.

Moreover, the filtering unit 122 filters the vital signals sensed according to the sensing mode determining in the sensing mode determining unit 118 to generate the potential signals matched to the determining body part and having the predetermined frequency.

For this, the vital potential sensing unit 120 may include a matching unit 124. The matching unit 124 includes matched vital signal information of matched with the determined results from the body part determining unit 116. In this case, the vital signal sensing unit 112 senses the vital signal shown in the vital signal information matched to the determined results. The matching unit 124 also includes information about filtering of each determination result of the body part determining unit 116. In this case, the filtering unit 122 filters the sensed vital signals of the vital signal sensing unit 112 according to the information matched with each of the determined results.

The vital signals sensed in the vital signal sensing unit 112 operating according to the sensing mode determining in the sensing mode determining unit 118 may be all the vital signals from in the sensed body parts.

In this case, the filtering unit 122 filters the sensed vital signals in order to generate potential signals having vital signals matched according to the determined result of the body part determining unit 116 and predetermined. The predetermined vital signals may be ECG signals, EMG signals, and PPF signals.

For this, the vital potential sensing unit 120 may further include a matching unit 124. The matching unit 124 includes information on the determined result of the body part determining unit 116 and the predetermined frequency matched to the determined result. Consequently, when the vital signal sensing unit 112 senses all the vital signals that can be sensed from the body part, the filtering unit 122 filters all of the sensed vital signals in order to generate potential signals having the frequency matched to the examining result and predetermined.

To calculate health indexes using the sensed vital signals from the health care apparatus, the behavior pattern of the examinee must be taken into consideration.

For example, the stress amount of the examinee may be calculated using the sensed ECG signals of the examinee taking a rest. Consequently, the value of the stress amount has less reliability when the examinee is exercising.

In the same manner, the behavior pattern of the examinee must be taken into consideration to sense the EMG signals to calculate the amount of consumed calories. For example, to calculate the amount of consumed calories when the examinee is riding a bicycle or skating, the EMG signals sensed in the muscles of the lower body of the examinee may be used. Consequently, the amount of calories calculated using the EMG signals sensed from the muscles of the lower body cannot indicate an accurate amount of consumed calories of the examinee who is exercising using the lower body. That is, in order to calculate an accurate amount of consumed calories of the examinee who is exercising using the lower body, the EMG signals sensed in the muscles of the lower body of the examinee must be used.

The health care apparatus according to the current embodiment of the present invention senses a current behavior pattern of the examinee without any information about the behavior pattern of the examinee and uses the vital potential sensing unit 120 to sense potential signals appropriate for the sensed behavior pattern.

Therefore, the potential signals refer to the vital signals having a frequency band corresponding to the body part determined by the body part determining unit 116 among the vital signals that can be sensed from the examinee, or the vital signals having the frequency band corresponding to the result sensed in the motion sensing unit 130.

How the vital signal sensing unit 120 senses the vital signals having the frequency band corresponding to the body part determined by the body part determining unit 116 among the vital signals that can be sensed from the examinee as potential signals has been described above. Hereinafter, it will be described how the vital potential sensing unit 120 senses the vital signals having the frequency band corresponding to the result sensed by the motion sensing unit 130 among the vital signals that can be sensed from the examinee as potential signals.

The vital signal sensing unit 112 responds to the result sensed by the motion sensing unit 130 to sense the vital signals of the examinee.

The vital signals sensed by the vital signal sensing unit 112 may be all the vital signals that can be sensed from the sensed the body parts. That is, the vital signal sensing unit 112 can sense all the vital signals that can be sensed from the sensed body parts when the motion sensing unit 130 senses any behavior pattern.

The vital signals sensed by the vital signal sensing unit 112 may be part of the vital signals that can be sensed from the sensed body parts. That is, the vital signal sensing unit 112 can sense one or more vital signals which are matched to the sensed behavior pattern of the motion sensing unit 130 and predetermined.

For example, if the motion sensing unit senses that the examinee is taking a rest, the vital signal sensing unit 112 may sense the ECG signal from the examinee. If the motion sensing unit 130 senses that the examinee is exercising using the lower part of the body, the vital signal sensing unit 112 may sense the EMG signal from muscles of the lower body of the examinee.

The filtering unit 122 responds to the result sensed by the motion sensing unit 130 to filter the vital signals sensed by the vital signal sensing unit 112 and outputs the filtering result as a potential signal.

When all of the vital signals that can be sensed from the sensed body parts are sensed by the vital signal sensing unit 112, the filtering unit 122 filters the sensed vital signals to generate potential signals having the predetermined vital signals matched to the behavior pattern sensed by the motion sensing unit 130. The vital signals may be ECG signals and EMG signals, etc.

For this, the vital potential sensing unit 120 may further include a matching unit 124. The matching unit 124 includes the result sensed by the motion sensing unit 130 and information of the vital signals which are matched to the sensed result and predetermined. Accordingly, the vital signal sensing unit 112 reads from the matching unit 124 the information on the vital signals matched to the result sensed by the motion sensing unit 130, and senses the vital signals in the read information.

The filtering unit 122 may filter the filtered vital signals again in order to generate potential signals having a frequency matched to the behavior pattern sensed in the motion sensing unit 130 and predetermined.

When some of the vital signals among the vital signals that can be sensed from the sensed body parts are sensed by the vital signal sensing unit 112, the filtering unit 122 may filter the filtered vital signals in order to generate potential signals having a frequency matched to the behavior pattern and predetermined.

For this, the vital potential sensing unit 120 may further include a matching unit 124. The matching unit 124 includes the result sensed by the motion sensing unit 130 and information of the vital signals which are matched to the sensed result and predetermined. Accordingly, the filtering unit 122 reads from the matching unit 124 the information on the frequency matched to the result sensed by the motion sensing unit 130, and senses the vital signals in the read information.

For example, if an ECG signal is sensed by the vital signal sensing unit 112 and the motion sensing unit 130 senses that the examinee is taking a rest, the filtering unit 122 filters ECG signals with a frequency ranging from 0.1 Hz to 150 Hz and blocks the rest of the ECG signals to generate and output potential signals having a frequency ranging from 0.1 Hz to 150 Hz.

The signals output from the filtering unit 122, that is, the filtered vital signals, are the potential signals sensed by the vital potential sensing unit 120.

The analyzing unit 150 analyzes the sensed potential signals, and the health care index calculating unit 160 calculates the health care index using the analyzed result.

The analyzing unit 150 and the health care index calculating unit 160 may be formed in a single body or connected to each other in a network. That is, the analyzing unit 150 and the health care index calculating unit 160 may also be separated.

For example, the analyzing unit 150 may be attached to a body part of the examinee, and the health care index calculating unit 160 may be formed in a computer that the examinee's doctor uses. If the analyzing unit 150 and the health care index calculating unit 160 are connected in a network, the analyzed result of the analyzing unit 150 is transmitted to the health care index calculating unit 160.

For this, the transmitting unit 170 may be formed in the health care apparatus according to the current embodiment of the present invention. That is, the transmitting unit 170 transmits the analyzed result of the analyzing unit 150 to the health care index calculating unit 160 connected to the analyzing unit 150.

The user interface 180 displays at least one of the analyzed result of the analyzing unit 150 and the health index calculated from the health care index calculating unit 160.

The health state notifying unit 190 informs the examinee of the health index calculated from the health care index calculating unit 160. Specifically, the health state notifying unit 190 compares the calculated sum of the health index calculating unit 160 with a predetermined critical value and responds to the compared result to inform the examinee.

The critical value refers to the value indicating an abnormal state of the body of the examinee when a health index value is either greater, smaller, or equal to the critical value. For example, when the health index calculating unit 160 calculates a health index such as heart stress and the calculated heart stress exceeds the critical value, an exercising examinee should stop exercising. The health state notifying unit 190 compares the calculated heart stress with the critical value, and directs the examinee to stop exercising when the calculated heart stress exceeds the critical value.

The health state notifying unit 190 uses one of a visual path, a tactual path, and a hearing path to inform the examinee. For this, the health state notifying unit 190 may include a vibrating motor, a speaker, or a display panel.

For example, to inform an examinee who is exercising to stop exercising, the health state notifying unit 190 which has compared the calculated heart stress with the critical value may vibrate the vibrating motor, may make a sound with the speaker, or display a sign on the display panel.

The storing unit 195 stores one of the analyzed result of the analyzing unit 150 and the health index calculated from the health index calculated in the health index calculating unit 160.

Figure 2A:
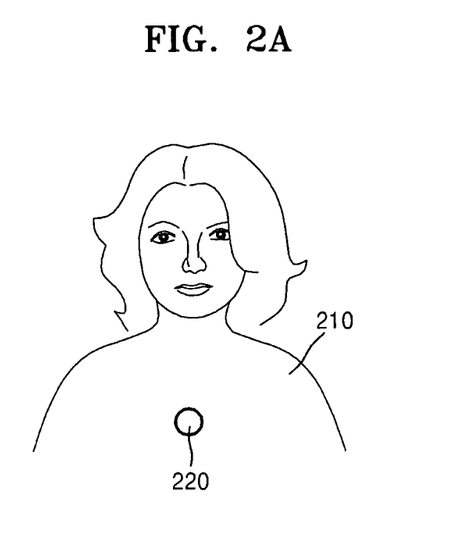
FIGS. 2A and 2B are reference drawings for explaining the health care apparatus of FIG. 1.
Figure 2B:
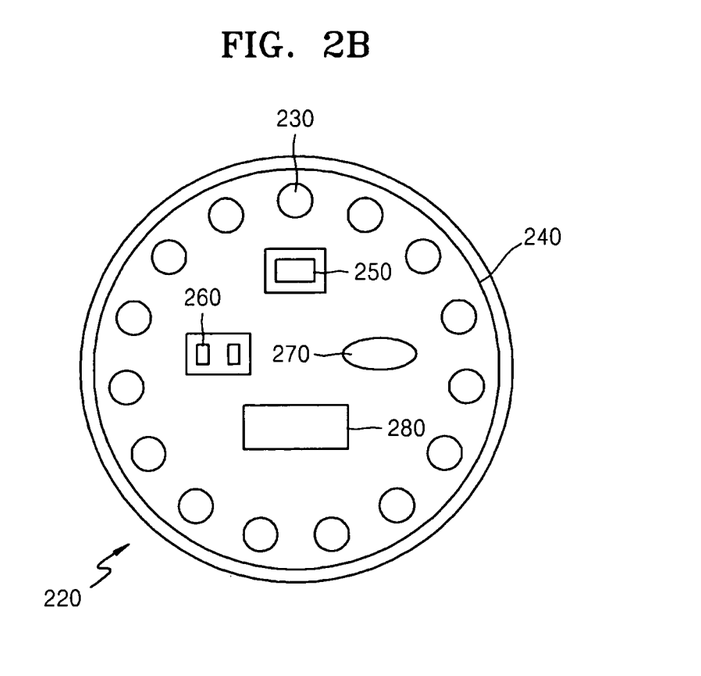

FIGS. 2A and 2B are reference drawings for explaining the health care apparatus of FIG. 1. As illustrated in FIGS. 2A and 2B, the sensing position determining unit 110 through the storing unit 195 can be formed in one body. In particular, the sensing position determining unit 110 through the analyzing unit 150 may be formed in one body.

FIG. 2A illustrates a health care apparatus according to an embodiment of the present invention. The sensing position determining unit 110, the vital potential sensing unit 120, the motion sensing unit 130, and the analyzing unit 150 may be disposed on, by way of a non-limiting example, a patch 220 as illustrated in FIG. 2B. The patch 220 may be, as a non-limiting example, a circle plate.

The health care apparatus may be formed on a medium which can be attached to or detached from the body of an examinee 210 like a patch as illustrated in FIG. 2B. The medium may also be, as a non-limiting example, a pendant of a necklace, which is not illustrated.

FIG. 2B illustrates the patch 220 including the health care apparatus of FIG. 2A. Reference numeral 230 denotes the vital signal sensing unit 112. If the vital signal sensing unit 112 is formed of a plurality of sensing devices, the reference numeral 230 denotes each of the sensing devices.

Reference numeral 240 denotes the transmitting unit 170, reference numeral 250 denotes the motion sensing unit 130, reference numeral 260 denotes the PPG sensor, and reference numeral 270 denotes a temperature sensor.

That is, the vital signal sensing unit 112 may generate a PPG signal or a core temperature. The core temperature refers to the temperature of a body part which is separated a predetermined distance from the outer skin of the body part to be examined. The distance may be predetermined and various.

If the vital signal sensing unit 112 senses PPG, the health index calculating unit 160 can measure the oxygen saturation of the blood of the examinee 210. Furthermore, if the vital signal sensing unit 112 senses both the PPG and the ECG signals, the health index calculating unit 160 can calculate the blood pressure of the examinee.

Reference numeral 280 denotes a controlling unit, and the controlling unit 280 controls the operation of both the vital signal sensing unit 230 through the temperature sensor 270.

Figure 3A:
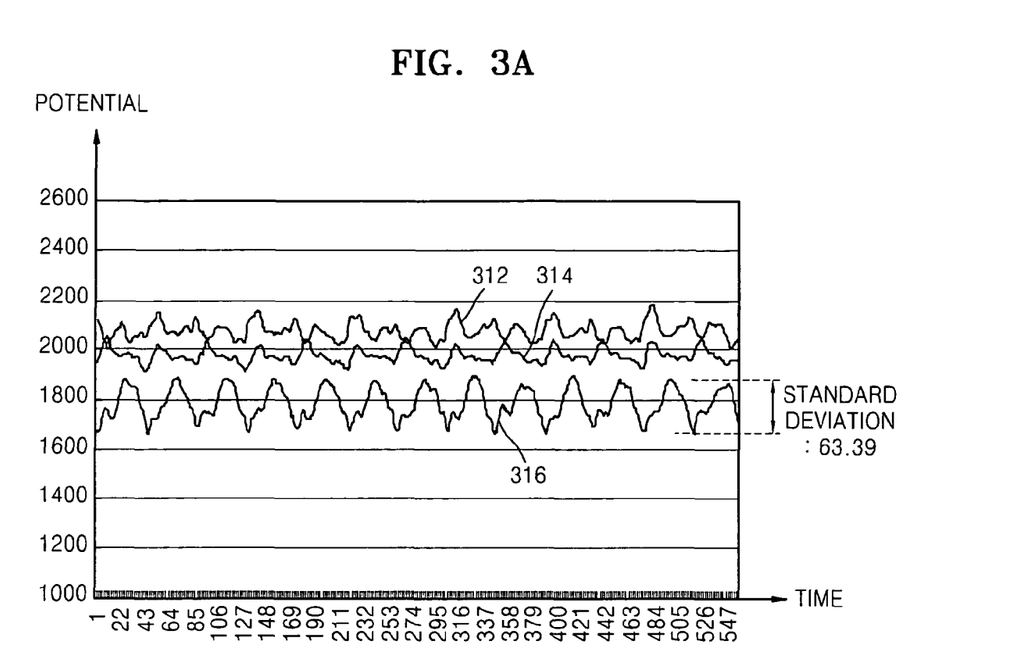
FIGS. 3A through 3C are reference drawings for explaining a body part examining process of a sensing position determining unit 110 of FIG. 1 according to an embodiment of the present invention.
Figure 3B:
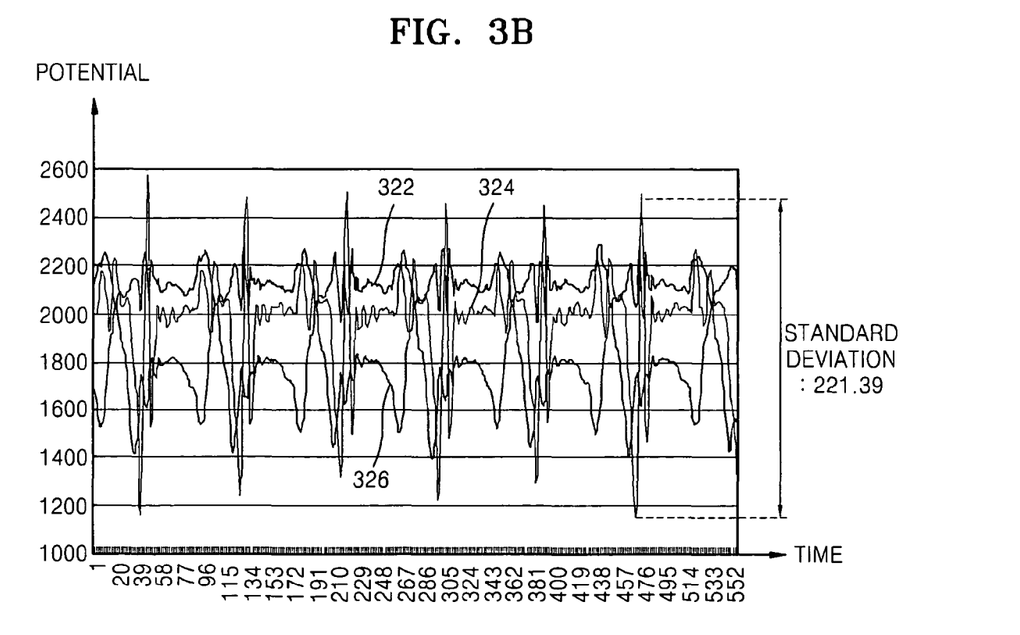
Figure 3C:
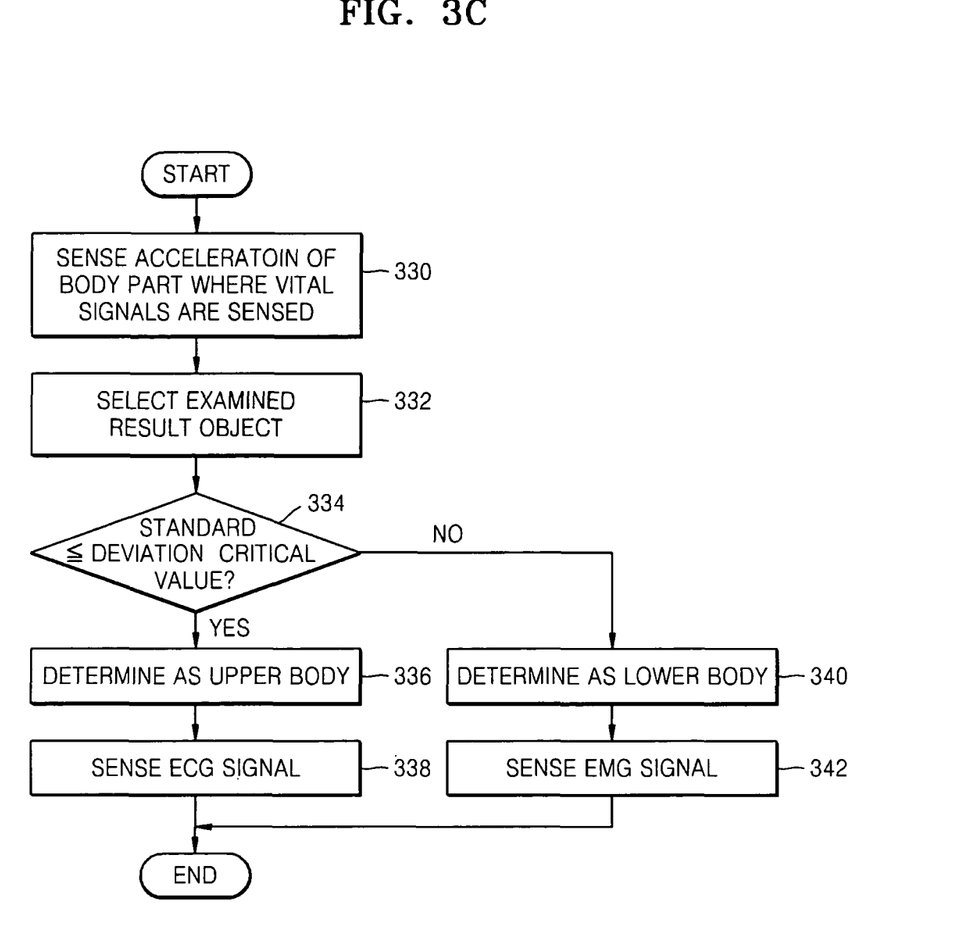

FIGS. 3A through 3C are reference drawings for explaining the determining process of a body part of the sensing position determining unit 110 of FIG. 1 according to an embodiment of the present invention Specifically, FIG. 3A is a time graph of the acceleration sensed by the motion sensing unit 130 when the health care apparatus in a device is attached to the chest of the examinee. Likewise, FIG. 3B is a time graph of the acceleration sensed by the motion sensing unit 130 when the health care apparatus in a device is attached to a thigh of the examinee. The x-axis of both FIGS. 3A and 3B is time, and the y-axis is the potential value sensed by the acceleration sensor included in the motion sensing unit 130.

FIG. 3C is a flowchart for explaining the body part determining process of the sensing position determining unit 110. The process includes sensing the acceleration of the body parts (operation 330) and determining whether the sensed result is predetermined, determining the body parts according to the determined result and sensing the vital signals corresponding to the determined results (operations 332, 334, 336, 338, 340, and 342).

The motion sensing unit 130 senses the acceleration of the body parts where vital signals are sensed in operation 330. At this point, the sensed acceleration is expressed in potential values over time as illustrated in FIGS. 3A through 3C.

The acceleration of the body parts where the vital signals are sensed is figured out by determining the acceleration of the body parts in x, y and z directions together.

The acceleration sensed by the motion sensing unit 130 is expressed in three timing plots 312, 314, and 316 in FIG. 3A, and in FIG. 3B as timing plots 322, 324, and 326.

The examining unit 114 selects the timing plot with the greatest standard deviation of the potential values to be examined in operation 332.

After operation 332, in operation 334, the examining unit 114 judges whether the standard deviation of the potential value of the selected timing plot is greater than the critical value. The critical value may be predetermined.

When the examining unit 114 determines that the standard deviation of the potential value of the selected timing plot is not greater than the critical value, the body part determining unit 116 determines that the body part where the vital signal is sensed is in the upper body in operation 336. Here, the vital signal sensing unit 112 senses the ECM signal in the body part in operation 338.

On the other hand, when the examining unit 114 determines that the standard deviation of the potential value is greater than the critical value in operation 334, the body part determining unit 116 determines that the body part where the vital signal is sensed is in the lower body in operation 340. Here, the vital signal sensing unit 112 senses the EMG signal in the body part in operation 342.

Figure 4:
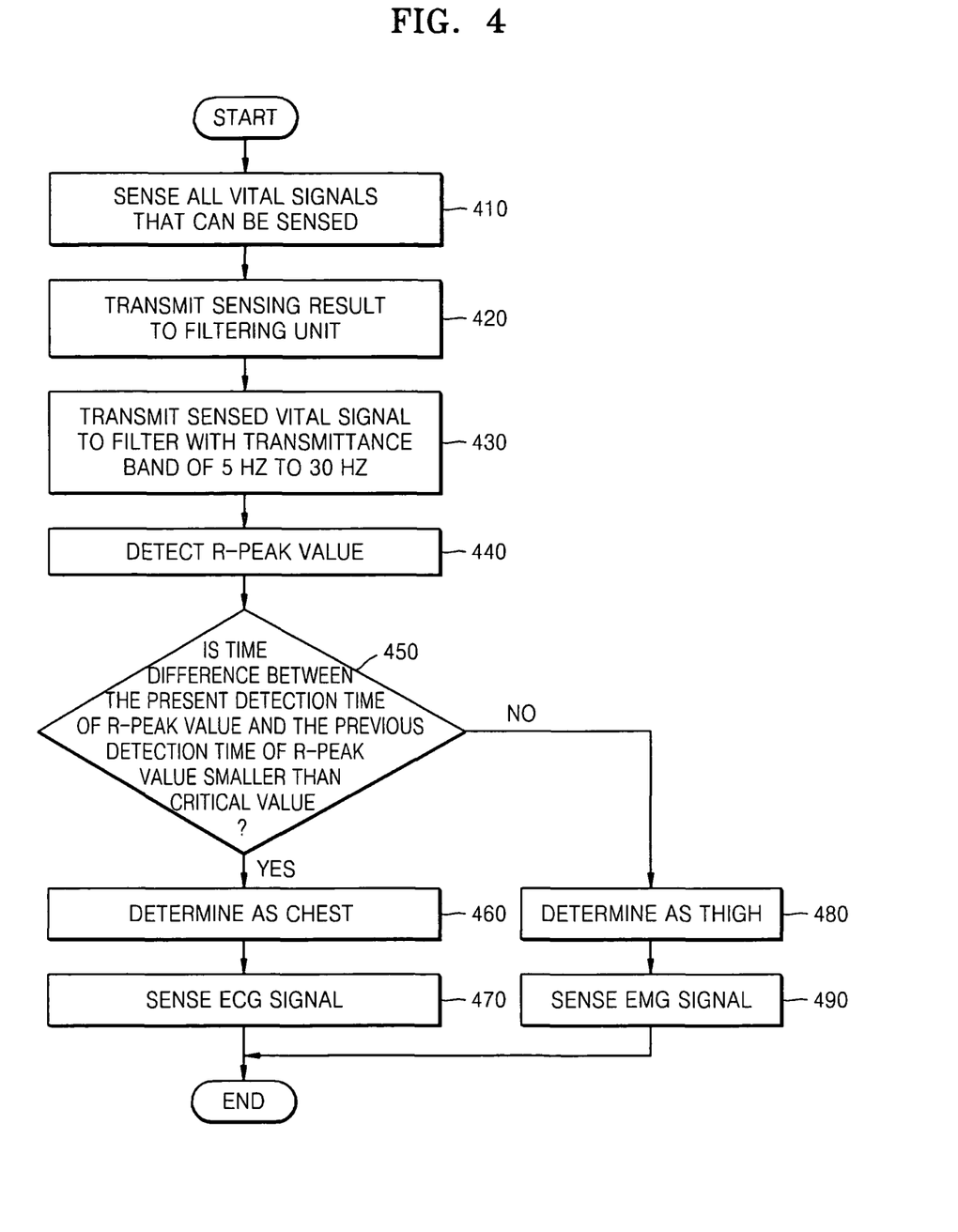
FIG. 4 is a flowchart illustrating the body part examining process of the sensing position determining unit 110 of FIG. 1 according to an embodiment of the present invention.

FIG. 4 is a flowchart for explaining the body part determining process of the sensing position determining unit 110 of FIG. 1. The process includes examining whether the predetermined vital signal is sensed in the body part (operations 410, 420, 430, 440, and 450) and determining the body parts according to the determined result and sensing the vital signals corresponding to the determined result (operations 460, 470, 480, and 490).

The vital signal sensing unit 112 senses all of the vital signals that can be sensed from the body parts where the vital signals are sensed in operation 410, and transmits the sensed vital signals to the filtering unit 122 in operation 420.

The sensed vital signals are mixed with ECG signals and EMG signals, etc., and if the health care apparatus is attached to the chest, the ECG signals sensed in operation 410 are prominent compared to other signals such as EMG signals. If the health care apparatus is attached to a thigh, the EMG signals sensed in operation 410 are prominent compared to other signals such as EMG signals.

After operation 420, the filtering unit 122 filters the sensed vital signals through a filter having a transmittance frequency band ranging from 5 Hz to 30 Hz which an R-peak signal of the ECG signal can have in operation 430.

After operation 430, the vital signal sensing unit 112 senses the R-peak value from the filtered vital signal in operation 440. The examining unit 114 judges whether the time difference between the present time point of the detected R-peak value and the time point of the detected R-peak value just before is smaller than the critical value in operation 450. Here, the critical value may be predetermined.

When the examining unit 114 judges that the time difference between the present time point of the detected R-peak value and the time point of detected R-peak value just before is smaller than the critical value, the body part determining unit 116 determines that the body part where the vital signals are sensed is the upper part of the body in operation 460. Here, the vital signal sensing unit 112 senses the ECG signals in the body part in operation 470.

On the other hand, if the examining unit 114 judges that the time difference between the present time point of the detected R-peak value and the time point of the R-peak value detected just before is greater than the critical value the body part determining unit 116 judges that the body part where the vital signals are sensed is the lower body in operation 480. Here, the vital signal sensing unit 112 senses the EMG signals in the body part in operation 470.

FIGS. 5A through 5E are reference drawings for explaining a process of calculating the stress amount of the examinee using the health care apparatus according to an embodiment of the present invention.

Figure 5A:
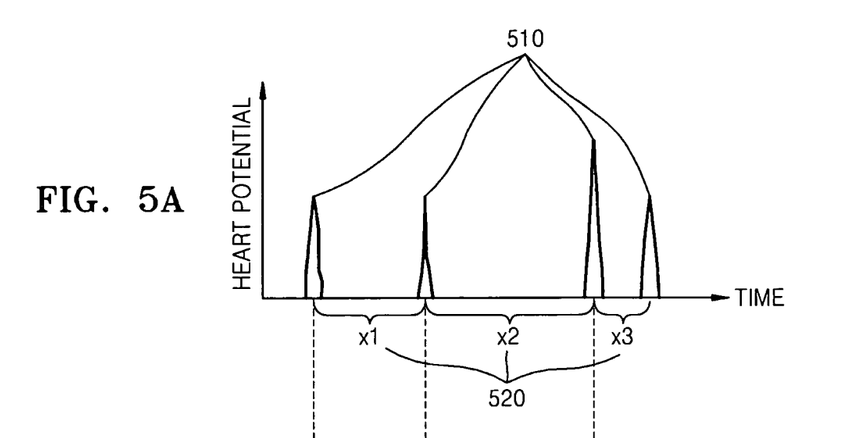
FIGS. 5A through 5E are reference drawings for explaining a process of calculating the stress amount of the examinee using the health care apparatus according to an embodiment of the present invention.

Specifically, FIG. 5A is a time graph illustrating the potential of the R-peak value 510 sensed from the examinee over time. Values x1, x2, and x3 (520) refer to R-R intervals (RRI). RRI refers to an interval between the peaks on a time axis.

Figure 5B:
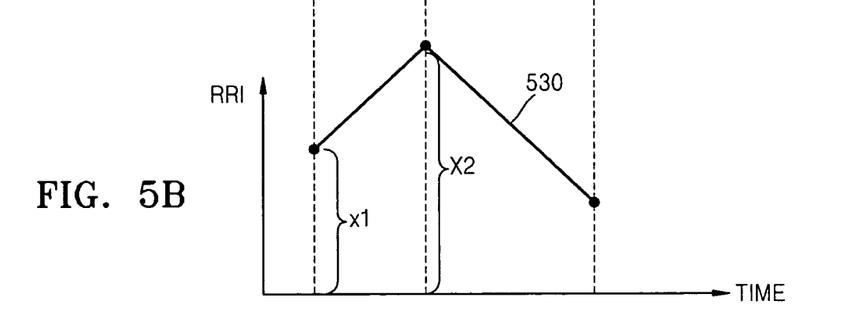

FIG. 5B is a time graph 530 illustrating the RRI values x1, x2, and x3 of FIG. 5A over time. Furthermore, FIGS. 5C and 5D are time graphs illustrating the time graph of FIG. 5B in large scale.

Figure 5C:
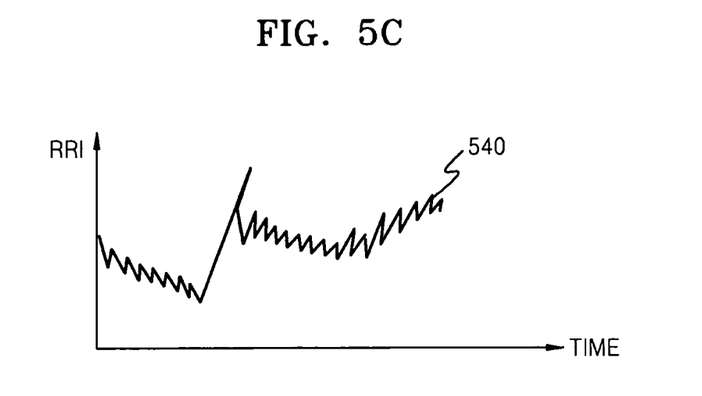
Figure 5D:
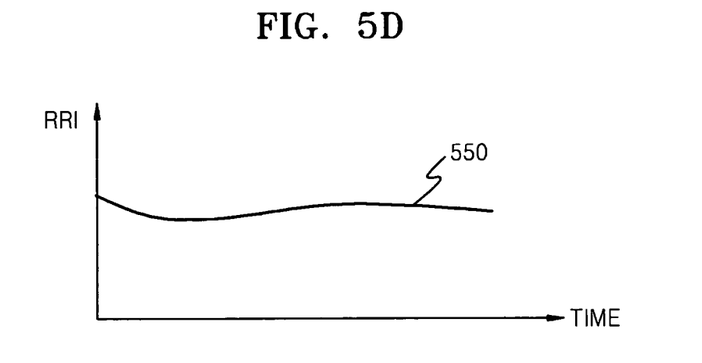

The time graph 540 of FIG. 5C is more random than the time graph 550 of FIG. 5D, and the examinee from whom the time graph 540 of FIG. 5C is sensed is healthier than the examinee from whom the time graph 550 of FIG. 5D is sensed.

Figure 5E:
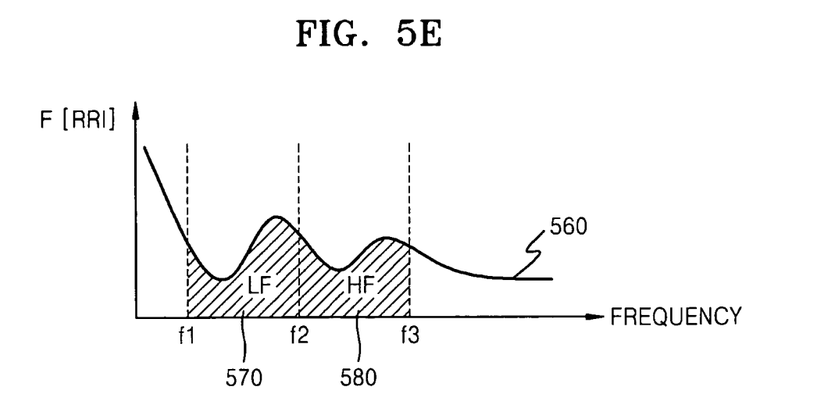

When the RRI signals of FIGS. 5C and 5D are Fourier transformed, a time graph 560 of FIG. 5E can be generated. Values f1, f2, and f3 may be 0.04 Hz, 0.1 Hz, and 0.5 Hz, respectively.

LF can be defined as in Equation 1.

$$LF = \int_{f1}^{f2} F[RRI(t)]df \quad \text{[Equation 1]}$$

Likewise, HF can be defined as in Equation 2.

$$HF = \int_{f2}^{f3} F[RRI(t)]df \quad \text{[Equation 2]}$$

LF is mainly affected by a sympathetic nervous system, and HF is mainly affected by a parasympathetic nervous system. Accordingly, HF/LF denotes whether the body and mind of the examinee are in a stable state.

For example, HF/LF=⅔ denotes that the body and mind of the examinee is in a stable state. As the health index calculating unit 160 calculates the amount of stress the examinee has at the moment, the health index calculating unit 160 can calculate the value of HF/LF and ⅔ is the critical value.

Specifically, the health state notifying unit 160 compares the HF/LF calculated by the health index calculating unit 160 with ⅔, and if the comparison result exceeds ⅔, the health state notifying unit 190 can inform the examinee that the examinee is nervous. If the comparison result is equal to or less than ⅔, the health state notifying unit 190 informs the examinee that the examinee is in a stable state.

Figure 6:
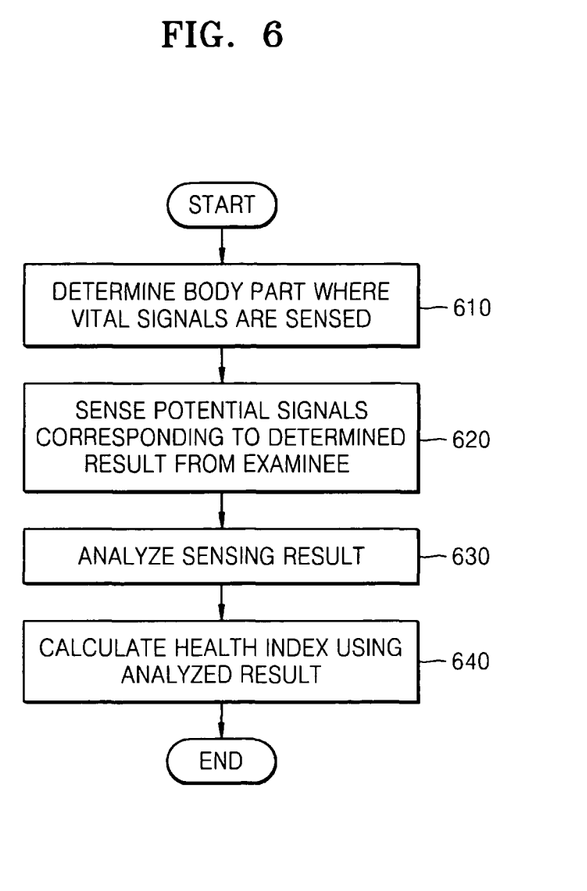
FIG. 6 is a flowchart illustrating a method of providing health care according to an embodiment of the present invention.

FIG. 6 is a flowchart for explaining a method of providing health care according to an embodiment of the present invention. The method includes determining body parts where vital signals are sensed and sensing potential signals corresponding to the determined result in operations 610 and 620, and analyzing the sensed result and using the analyzed result to calculate health indexes in operations 630 and 640.

The sensing position determining unit 110 determines the body parts where vital signals are sensed in operation 610, and the vital signal potential sensing unit 120 senses the potential signals corresponding to the determined result from the examinee in operation 620.

The analyzing unit 150 analyzes the sensed potential signals in operation 630, and the health index calculating unit 160 calculates the health indexes using the analyzed result in operation 640.

Figure 7:
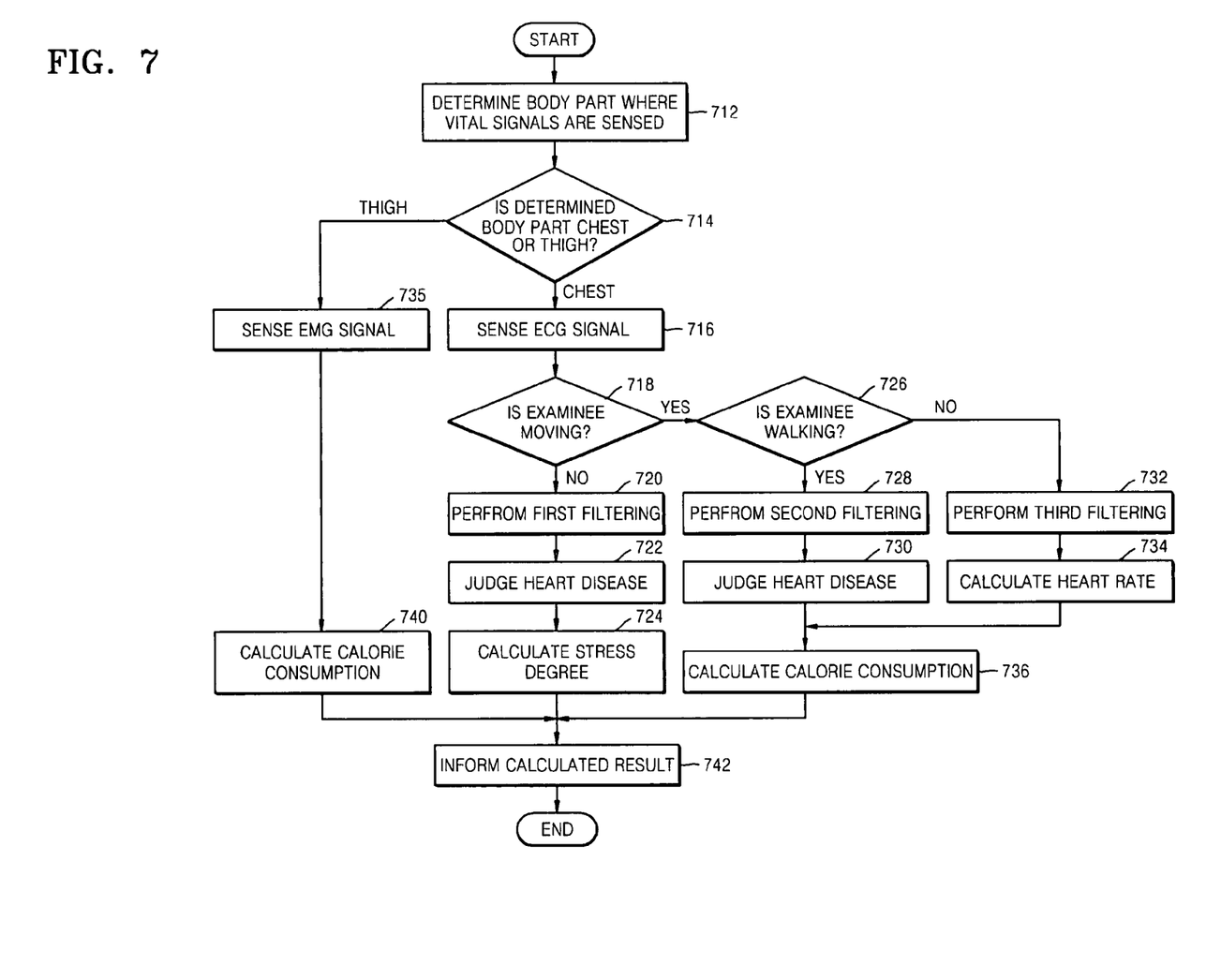
FIG. 7 is a flowchart illustrating a method of providing health care according to another embodiment of the present invention.

FIG. 7 is a flowchart for explaining a method of providing health care according to another embodiment of the present invention. The method includes determining body parts where vital signals are sensed and sensing potential signals corresponding to the determined results from the examinee in operations 712, 714, 716, and 735, and analyzing the sensed results and using the analyzed result to calculate health indexes and inform the examinee of the calculated result in operations 718 through 736 and 740 through 742.

The sensing position determining unit 110 of FIG. 1 determines the body parts where vital signals are sensed in operation 712. If the body part is determined to be the chest in operation 712, the vital signal sensing unit 112 senses ECG signals in the body part in operation 716.

After operation 716, the filtering unit 122 filters the sensed ECG signals according to the sensed result of the motion sensing unit 130.

Specifically, if the motion sensing unit 130 judges that the examinee is taking a rest in operation 718, the filtering unit 122 performs a first filtering in operation 720. For simplicity of explanation, in the first filtering process, frequencies ranging from 0.1 Hz to 15 Hz are assumed to be transmitted. Then all of P, Q, R, S, and T waves of the ECG are transmitted. The first filtered vital signal is a potential signal.

After operation 720, the analyzing unit 150 analyzes the first filtered vital signals and the health index calculating unit 160 uses the analyzed result to judge whether the heart rate of the examinee has any problem. Furthermore, the health index calculating unit 160 uses the analyzed result to calculate the amount of stress the examinee has.

If the motion sensing unit 130 senses that the examinee is walking in operation 726, the filtering unit 122 performs a second filtering of the sensed ECG signals in operation 728. For simplicity of explanation, in the second filtering process frequencies ranging from 1 Hz to 60 Hz are assumed to be transmitted. All of the P, Q, R, S, and T waves of the ECG signals are transmitted here. The second filtered vital signal is a potential signal.

After operation 728, the analyzing unit 150 analyzes the second filtered vital signals and the health index calculating unit 160 uses the analyzed result to judge whether the heart rate of the examinee has any problem. Furthermore, the health index calculating unit 160 uses the analyzed result to calculate the amount of consumed calories of the examinee in operation 736.

If the motion sensing unit 130 senses that the examinee is running in operation 726, the filtering unit 122 performs a third filtering of the sensed ECG signals in operation 732. For simplicity of explanation, in the third filtering process, frequencies ranging from 5 Hz to 30 Hz are assumed to be transmitted. Here, Q, R, and S waves are transmitted. The third filtering vital signal is a potential signal.

After operation 732, the analyzing unit 150 analyses the third filtered vital signal and the health index calculating unit 160 calculates the heart rate of the examinee in operation 734. Furthermore, the health index calculating unit 160 uses the analyzed result to calculate the amount of consumed calories of the examinee in operation 740.

After operations 724, 736, and 740, the health state notifying unit 170 informs the examinee of the calculated health index.

Embodiments of the present invention can also be embodied as computer readable codes on a computer readable recording medium. The computer readable recording medium may be any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion.

As described above, in the health care apparatus and method according to the above-described embodiments of the present invention, body parts where vital signals are sensed are determined and potential signals corresponding to the determined result is sensed from the examinee, and the sensed result is analyzed to determine the health state of the examinee. Accordingly, even without information of the body parts to which the health care apparatus is attached, the health care apparatus determines the body part by itself and senses potential signals corresponding to the body parts to calculate reliable measurements. Furthermore, the health care apparatus of the present invention can be easily attached to the body compared to a conventional health care apparatus, and can calculate the health index reflecting the present behavior pattern of the examinee. The health care apparatus of the above-described embodiments of the present invention can also figure out the health state of local body parts of the examinee and inform the examinee about the calculated health indexes on a real-time basis Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A health care apparatus comprising:
   a sensing position determining unit to determine a body part of an examinee where vital signals of the examinee are sensed;
   a vital potential sensing unit configured to sense different potential signals of the examinee based on the determined body part; and
   an analyzing unit to analyze the potential signals,
   wherein the sensing position determining unit comprises:
   an examining unit to examine whether an acceleration of the body part meets a predetermined magnitude; and
   a body part determining unit to determine the body part in response to an examined result.

2. The apparatus of claim 1, further comprising a health index calculating unit to calculate a desired health index using a result from the analyzing unit, the health index being an index indicating a body state of the examinee.

3. The apparatus of claim 2 further comprising a user interface unit providing a user interface displaying at least one of the analyzed result and the calculated health index.

4. The apparatus of claim 2, further comprising a health state notifying unit that functions corresponding to the calculated health index to inform the examinee about a health state of the examinee.

5. The apparatus of claim 4, wherein the health state notifying unit informs the examinee about the health state of the examinee using a visual path, a hearing path, or a tactual path.

6. The apparatus of claim 2, wherein the health index is one selected from the group consisting of a heart rate, a heart stress, a balance of the autonomous nervous system, an amount of consumed calories, a blood pressure and a core temperature.

7. The apparatus of claim 1, wherein the sensing position determining unit comprises:
   an examining unit to examine whether a predetermined vital signal is sensed in the body part; and
   a body part determining unit to determine the body part in response to the examined result.

8. The apparatus of claim 1, wherein the vital potential sensing unit senses the vital signals of the examinee based on the determined body part.

9. The apparatus of claim 1, wherein the vital potential sensing unit comprises:
   a vital signal sensing unit to sense the vital signals of the examinee in response to the determined body part; and
   a filtering unit to filter the sensed vital signals in response to the determined body part and to output the filtered vital signals as the potential signals.

10. The apparatus of claim 9, wherein the vital signal sensing unit senses electrocardiogram (ECG) signals or electromyogram (EMG) signals of the examinee in response to the determined body part.

11. The apparatus of claim 1, wherein the vital potential sensing unit is formed of one or more sensing devices attached to the body of the examinee.

12. The apparatus of claim 11, wherein the one or more sensing devices are formed in a single body or separately connected to each other in a network.

13. The apparatus of claim 1, wherein the potential signal is a vital signal having a frequency band corresponding to the determined body part among the vital signals that can be sensed from the examinee.

14. An apparatus comprising;
   a sensing position determining unit to determine a body part of an examinee where vital signals of the examinee are sensed;
   a vital potential sensing unit to sense potential signals of the examinee corresponding to the determined body part; and
   an analyzing unit to analyze the sensed potential signals,
   wherein the vital potential sensing unit comprises;
   a vital signal sensing unit to sense the vital signals of the examinee in response to the determined body part; and
   a filtering unit to filter the sensed vital signals in response to the determined body part and to output the filtered vital signals as the potential signals,
   wherein the vital potential sensing unit further comprises a sensing mode determining unit to determine sensing modes in response to the determined body part, and
   wherein the vital signal sensing unit and the filtering unit operate according to the determined sensing modes.

15. An apparatus comprising,
   a sensing position determining unit to determine a body part of an examinee where vital signals of the examinee are sensed;
   a vital potential sensing unit to sense potential signals of the examinee corresponding to the determined body part; and
   an analyzing unit to analyze the sensed potential signals,
   wherein the vital potential sensing unit comprises;
   a vital signal sensing unit to sense the vital signals of the examinee in response to the determined body part; and
   a filtering unit to filter the sensed vital signals in response to the determined body part and to output the filtered vital signals as the potential signals,
   wherein the vital potential sensing unit further comprises a matching unit in which information about the vital signals is matched to the determined body part, and
   wherein the vital signal sensing unit senses the vital signals expressed in the vital signal information matched to the determined body part.

16. An apparatus, comprising:
   a sensing position determining unit to determine a body part of an examinee where vital signals of the examinee are sensed;
   a vital potential sensing unit to sense potential signals of the examinee corresponding to the determined body part; and
   an analyzing unit to analyze the sensed potential signals,
   wherein the vital potential sensing unit comprises;
   a vital signal sensing unit to sense the vital signals of the examinee in response to the determined body part; and
   a filtering unit to filter the sensed vital signals in response to the determined body part and to output the filtered vital signals as the potential signals,
   wherein the vital potential sensing unit further comprises a matching unit in which information about the filtering is matched to the determined body part, and the filtering unit filters the sensed vital signals according to the filtering information matched to the determined body part.

17. A non-transitory computer-readable medium storing a computer program performing a health care method comprising:
   determining a body part of an examinee where vital signals of the examinee sensed;
   sensing different potential signals of the examinee based on the determined body part; and
   analyzing the potential signals,
   wherein determining the body part comprises:
   examining whether an acceleration of the body part meets a predetermined magnitude; and
   determining the body part in response to an examined result.

* * * * *